US00PP23438P2

(12) United States Plant Patent
van Kleinwee

(10) Patent No.: US PP23,438 P2
(45) Date of Patent: Feb. 26, 2013

(54) ***OSTEOSPERMUM* PLANT NAMED 'OSTZ0002'**

(50) Latin Name: *Osteospermum ecklonis*
Varietal Denomination: OSTZ0002

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,865

(22) Filed: Oct. 31, 2011

(51) Int. Cl.
*A01H 5/00* (2006.01)

(52) U.S. Cl. ..... Plt./360

(58) Field of Classification Search ..... Plt./360
See application file for complete search history.

*Primary Examiner* — Kent L Bell
(74) *Attorney, Agent, or Firm* — Joshua L. Price

(57) ABSTRACT

A new *Osteospermum* plant named 'OSTZ0002' particularly distinguished by the large dark eyed two-toned yellow and yellow-orange inflorescences, held well above the foliage, medium-deep green foliage, medium sized and semi-upright plant habit with fair branching.

1 Drawing Sheet

Latin name of the genus and species of the plant claimed: *Osteospermum ecklonis*.

Varietal denomination: 'OSTZ0002'.

BACKGROUND OF THE NEW PLANT

The present invention comprises an *Osteospermum*, botanically known as *Osteospermum ecklonis*, and hereinafter referred to by the variety name 'OSTZ0002'.

'OSTZ0002' is a product of a planned breeding program. The new cultivar has large dark eyed two-toned yellow and yellow-orange inflorescences held well above the foliage, medium-deep green foliage, medium sized and semi-upright plant habit with fair branching.

'OSTZ0002' originated from an open pollination occurring in the summer of 2006 in a controlled environment in Enkhuizen, Netherlands. The female parent was an unpatented plant identified as '7-47-2', having yellow inflorescences and a more mounding and less upright plant habit.

The male parent of 'OSTZ0002' is not known.

The resulting seeds were sown in Enkhuizen, Netherlands in March 2007. 'OSTZ0002' was selected as one flowering plant within the progeny of the stated cross in August 2007.

The first act of asexual reproduction of 'OSTZ0002' was accomplished when vegetative cuttings were propagated from the initial selection in October 2007 in a controlled environment in Enkhuizen, Netherlands.

BRIEF SUMMARY OF THE INVENTION

Horticultural examination of plants grown from cuttings of the plant initiated in the spring of 2008 in Enkhuizen, Netherlands, and continuing thereafter, has demonstrated that the combination of characteristics as herein disclosed for 'OSTZ0002' are firmly fixed and are retained through successive generations of asexual reproduction.

'OSTZ0002' has not been observed under all possible environmental conditions. The phenotype may vary significantly with variations in environment such as temperature, light intensity and day length.

Plant Breeder's Rights for this cultivar have been applied in Canada on Dec. 24, 2010, #10-7142 and at the Community Plant Variety Office on Oct. 15, 2010, #2010/2179. 'OSTZ0002' has not been made publicly available more than one year prior to the filing of this application.

The following traits have been repeatedly observed and are determined to be basic characteristics of the new variety. The combination of these characteristics distinguishes this *Osteospermum* as a new and distinct variety.

BRIEF DESCRIPTION OF THE PHOTOGRAPHS

The accompanying photographic drawing shows typical flower and foliage characteristics of 'OSTZ0002' with colors being as true as possible with an illustration of this type. The photographic drawing shows a flowering plant of the new variety, and a close-up of the inflorescences.

DETAILED BOTANICAL DESCRIPTION

The aforementioned photographs were taken on Apr. 28, 2011, from plants grown in a greenhouse trial in Andijk, Netherlands. These plants were grown in 10.5 cm pots and were approximately 3 months of age.

The plant descriptions and measurements were taken in Andijk, Netherlands in mid-May 2011 using 12 week old greenhouse grown plants. Culture of these plants had started in mid February 2011 with planting rooted cuttings into 10.5 cm pots and growing them at a minimum temperature of 16-18° C. in the greenhouse.

Color references are made to The Royal Horticultural Society Colour Chart (R.H.S.) 2001

DIFFERENCES BETWEEN THE NEW VARIETY 'OSTZ0002' AND A SIMILAR VARIETY

| | 'OSTZ0002' | 'Tra Yelbic' (U.S. Plant Pat. No. 20,178) |
|---|---|---|
| Ray floret color: | Yellow/yellow-orange | White/yellow |
| Quantity of ray florets: | Fewer | More |

-continued

| DIFFERENCES BETWEEN THE NEW VARIETY 'OSTZ0002' AND A SIMILAR VARIETY | | |
|---|---|---|
| | 'OSTZ0002' | 'Tra Yelbic' (U.S. Plant Pat. No. 20,178) |
| Inflorescence diameter: | Larger | Smaller |
| Foliage color: | Somewhat darker | Lighter |

Plant:

*Plant habit*.—Initially appears more semi-upright and later becoming more spreading, moderately tight canopy of medium branching, with the inflorescences held well above the foliage on strong peduncles.

*Plant height* (*without inflorescences*).—12.0-16.0 cm.

*Plant height* (*inflorescence included*).—17.0-19.0 cm.

*Plant width*.—24.0-27.0 cm.

Roots:

*Number of days to initiate and develop roots*.—21-25 days at about 22 degrees C.

*Type*.—Fine, fibrous, free branching.

*Color*.—RHS N155B but whiter.

Foliage:

*Arrangement*.—Alternate, simple leaves.

*Immature, leaf color, upper surface*.—RHS 143A. Lower surface: RHS 143C.

*Mature, leaf color, upper surface*.—RHS 137A, sometimes a little darker. Lower surface: RHS 138A.

*Length*.—4.5-5.5 cm.

*Width*.—1.1-1.4 cm.

*Shape*.—Spathulate.

*Base shape*.—Attenuate.

*Apex shape*.—Obtuse.

*Margin*.—Moderately dentate. Texture, upper surface: Smooth, appears glabrous. Lower surface: Fine, short hair.

*Color of veins, upper surface*.—RHS 138A near base, for main part indistinct.

*Color of veins, lower surface*.—RHS 144A.

*Petiole color*.—RHS 138A for the upper surface; RHS 144A for the underside.

*Length*.—About 0.7-1.5 cm.

*Diameter*.—0.3 cm.

*Texture*.—Short hair along the edges.

Stem:

*Quantity of main branches per plant*.—9-11.

*Color of stem*.—RHS 143B mainly, occasionally a little anthocyanin blotches of about RHS 165A or RHS 152A.

*Stem length*.—About 13.0-18.0 cm.

*Stem diameter*.—0.3 cm.

*Length of internodes*.—0.5-2.0 cm.

*Texture*.—Sparse short hair.

Peduncle:

*Color of peduncle*.—RHS 143C.

*Length of peduncle*.—About 3.0-5.0 cm.

*Peduncle diameter*.—0.2 cm.

*Texture*.—Moderately dense with short hairs.

Inflorescence:

*Type*.—Capitulum (compositae-type), single inflorescences, borne terminally, with 1-2 whorls of ray florets.

*Quantity of inflorescences per plant*.—10-12 open flowers and additional buds.

*Lastingness of individual blooms on the plant*.—About one week depending on temperature.

*Fragrance*.—None.

Bud (just when opening/showing color):

*Color*.—About RHS 165A with stripes of RHS 164A.

*Length*.—1.8-2.2 cm.

*Width*.—0.9-1.1 cm.

*Shape*.—Ovate to elliptical.

Immature inflorescence:

*Diameter*.—About 4.5 cm.

*Color of ray florets*.—Mainly RHS 12A with RHS 163A at the apex.

*General color of 'disc' with disc florets still closed*.—Near RHS 200A.

Mature inflorescence:

*Shape*.—Inflorescences with the ray florets slanting somewhat upwards.

*Diameter of whole inflorescence*.—6.5-7.9 cm.

*Diameter of 'disc'*.—1.5-1.6 cm.

*Diameter of receptacle*.—About 1.0 cm at base of florets.

Ray florets:

*Average quantity of ray florets*.—18-21.

*Color of floret, upper surface*.—Mostly RHS 12A with RHS 22A at the apex; with weak hue of RHS 75A at the very base that is sometimes a blotch of about RHS N79D. Maturing to somewhat to RHS 8A with RHS 16B at the apex.

*Color of lower surface*.—RHS 164C with RHS 164A down the middle of petal.

*Length*.—3.0-3.8 cm.

*Width*.—0.8-0.9 cm.

*Shape*.—Ensiform or oblanceolate.

*Apex shape*.—Rounded, some slightly praemorse.

*Margin*.—Entire. Texture, upper surface: Glabrous; with hair (pappus) at base. Texture, lower surface: mostly smooth and glabrous, slightly protruding veins.

Disc florets:

*Average quantity of disc florets*.—About 40.

*Color of young* (*just before opening*) *floret at apex*.—RHS 200A.

*Color of open floret*.—RHS N155B with RHS 187A to RHS 187B apex.

*Length of floret*.—0.7-0.8 cm.

*Width at apex*.—0.2-0.3 cm.

*Apex shape*.—Acute, 5-pointed.

Phyllaries:

*Quantity of phyllaries*.—16-20.

*Color, outer surface*.—RHS 137B.

*Color, inner side*.—RHS 137D.

*Length*.—0.9-1.3 cm.

*Width*.—0.2 cm.

*Shape*.—Ligulate.

*Apex shape*.—Acute to acuminate.

*Base*.—Sessile, fused with receptacle.

*Margins*.—Entire.

*Texture outer surface*.—Rough with short hair.

*Texture inner surface*.—Glossy and glabrous.

Reproductive organs:

*Gynoecium*.—Pistil: One. Length: 0.8 cm. Style color: RHS 187A. Style length: 0.4 cm. Stigma color: RHS 187B. Stigma shape: Bi-lobed.

*Androecium*.—Stamina: Present in disc florets only, fused and forming a tube. Color of filaments: RHS N155B. Length filaments: 0.3 cm. Anther color: N187A at tip, fading towards base. Color of pollen: RHS 17B. Pollen amount: Normal.

Fertility/seed set: Has not been observed on this hybrid.

Disease/pest resistance: Has not been observed on this hybrid.

What is claimed is:

1. A new and distinct variety of *Osteospermum* plant named 'OSTZ0002' substantially as illustrated and described herein.

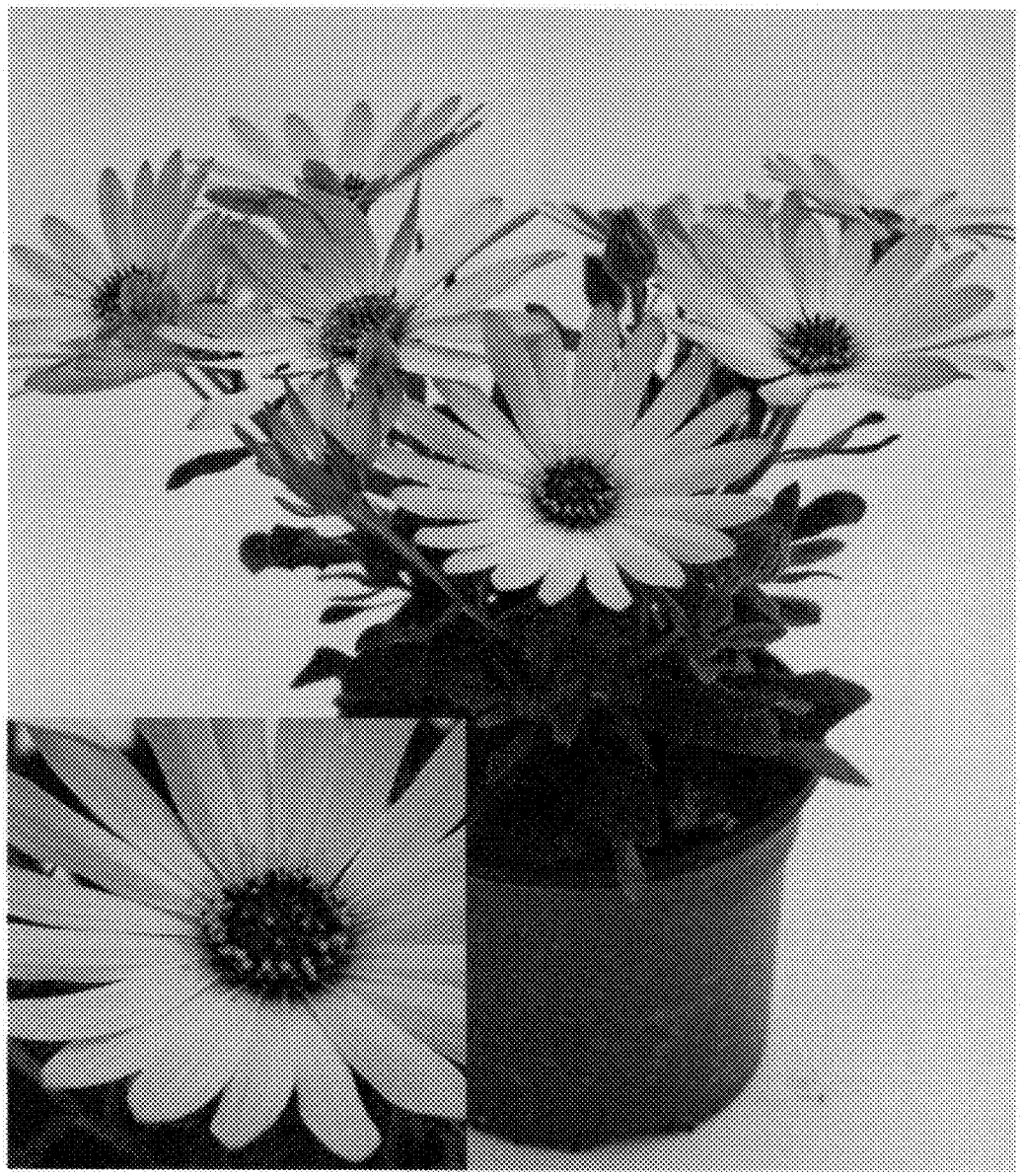

* * * * *